United States Patent
Baranowski (10) Patent No.: US 11,219,518 B2
(45) Date of Patent: Jan. 11, 2022

(54) OBLIQUE SEAM FOR REDUCED STENT GRAFT PACKING DENSITY IN DELIVERY SYSTEM

(71) Applicant: Medtronic Vascular, Inc., Santa Rosa, CA (US)

(72) Inventor: Ian Benjamin Baranowski, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 0 days.

(21) Appl. No.: 16/685,271

(22) Filed: Nov. 15, 2019

(65) Prior Publication Data

US 2021/0145565 A1 May 20, 2021

(51) Int. Cl.
*A61F 2/07* (2013.01)
*A61F 2/06* (2013.01)

(52) U.S. Cl.
CPC .......... *A61F 2/07* (2013.01); *A61F 2002/061* (2013.01); *A61F 2002/065* (2013.01); *A61F 2220/0075* (2013.01); *A61F 2250/0098* (2013.01)

(58) Field of Classification Search
None
See application file for complete search history.

(56) References Cited

U.S. PATENT DOCUMENTS

| | | | |
|---|---|---|---|
| 7,914,572 B2 | 3/2011 | Hartley et al. | |
| 8,778,008 B2 | 7/2014 | Amplatz et al. | |
| 9,180,030 B2 | 11/2015 | Brocker et al. | |
| 2003/0195614 A1* | 10/2003 | Ryan | A61F 2/07 623/1.16 |
| 2007/0010874 A1* | 1/2007 | Sun | A61F 2/07 623/1.35 |
| 2008/0046065 A1* | 2/2008 | Hartley | A61F 2/07 623/1.13 |

FOREIGN PATENT DOCUMENTS

| | | |
|---|---|---|
| AU | 2010201067 B1 | 6/2011 |
| EP | 3135248 A1 | 3/2017 |
| WO | 2006034276 A1 | 3/2006 |

\* cited by examiner

*Primary Examiner* — Leslie Lopez
(74) *Attorney, Agent, or Firm* — Brooks Kushman P.C.

(57) ABSTRACT

An endovascular stent graft for treatment of a blood vessel is provided. The stent is configured to be inserted into the blood vessel while in a radially-contracted configuration, and may be opened into a radially-expanded configuration once properly located within the blood vessel. The stent graft includes a main body having a proximal end and a distal end. The distal end of the main body is connected to a first leg and a second leg. A first plurality of stitching extends along a first seam path and connects the main body to the first leg, while a second plurality of stitching extends along a second seam path and connects the main body to the second leg. At least one of the first or second seam axes can be offset, in that the seam path does not extent perpendicular to a longitudinal axis of the stent graft.

20 Claims, 5 Drawing Sheets

FIG. 1

PRIOR ART

FIG. 2A

PRIOR ART

OBLIQUE SEAM FOR REDUCED STENT GRAFT PACKING DENSITY IN DELIVERY SYSTEM

TECHNICAL FIELD

The present disclosure generally relates to a stent graft for a medical procedure. The stent graft may include an oblique seam to reduce packaging density when the stent graft is in a compressed configuration.

BACKGROUND

Prostheses are implanted in blood vessels and other organs of living bodies. For example, prosthetic endovascular grafts constructed of biocompatible materials have been employed to replace or bypass damaged or occluded natural blood vessels. In general, endovascular grafts include a graft anchoring component that operates to hold a tubular graft component of a suitable graft material in its intended position within the blood vessel. The graft anchoring component typically includes one or more radially-compressible stents that are radially expanded in situ to anchor the tubular graft component to the wall of a blood vessel or anatomical conduit.

Rather than performing a traumatic and invasive open surgical procedure to implant a graft, endovascular grafts (e.g., stent grafts) may be deployed through a less invasive intraluminal delivery procedure. A lumen or vasculature may be accessed at a convenient and less traumatic entry point of the patient's body, and the stent graft may be routed through the vasculature to the site where the prosthesis is to be deployed. Intraluminal deployment typically uses a delivery catheter with tubes or shafts arranged for relative axial movement. For example, an expandable stent graft may be compressed and disposed within a distal end of an outer shaft of the delivery catheter fixed to an inner shaft. The delivery catheter may then be maneuvered, typically tracked through a body lumen until a distal end of the delivery catheter and the stent graft are positioned at the intended treatment site. The stent graft can then be deployed and radially expanded within the blood vessel.

SUMMARY

According to one embodiment, a stent graft is expandable from a radially-collapsed configuration to a radially-expanded position. The stent graft includes a main body extending along a main longitudinal axis and having a proximal end and a distal end. The stent graft also includes a first leg extending from the distal end of the main body, a second leg extending from the distal end of the main body, and a plurality of stitches coupling the main body to the first leg. The plurality of stitches forms a stitch path that extends in a direction oblique to the main longitudinal axis of the main body when the stent graft is in a preinstalled configuration prior to insertion into a body of a patient.

According to another embodiment, a stent graft includes a main body extending along a main longitudinal axis and having a proximal end and a distal end. The stent graft also includes a first leg attached to the distal end of the main body along a first seam that extends along a first seam path. The stent graft also includes a second leg attached to the distal end of the main body along a second seam that is continuous with the first seam and extends along a second seam path. The first seam path is oblique relative to the second seam path when the stent graft is in a preinstalled configuration prior to insertion into a body of a patient.

According to yet another embodiment, a stent graft includes a main body extending along a longitudinal axis when the stent graft is in a preinstalled configuration prior to insertion into a body of a patient. The stent graft includes a first leg extending axially from the axial end in a direction parallel to the longitudinal axis. The stent graft also includes a second leg extending axially from the axial end in a direction parallel to the longitudinal axis, the second leg being narrower than the first leg. The stent graft also includes a plurality of stitches coupling the main body to the first leg, the plurality of stitches forming a stitch path that extends in a direction oblique to the longitudinal axis.

DETAILED DESCRIPTION

Embodiments of the present disclosure are described herein. It is to be understood, however, that the disclosed embodiments are merely examples and other embodiments can take various and alternative forms. The figures are not necessarily to scale; some features could be exaggerated or minimized to show details of particular components. Therefore, specific structural and functional details disclosed herein are not to be interpreted as limiting, but merely as a representative basis for teaching one skilled in the art to variously employ the embodiments. As those of ordinary skill in the art will understand, various features illustrated and described with reference to any one of the figures can be combined with features illustrated in one or more other figures to produce embodiments that are not explicitly illustrated or described. The combinations of features illustrated provide representative embodiments for typical applications. Various combinations and modifications of the features consistent with the teachings of this disclosure, however, could be desired for particular applications or implementations.

Directional terms used herein are made with reference to the views and orientations shown in the exemplary figures. A central axis is shown in the figures and described below. Terms such as "outer" and "inner" are relative to the central axis. For example, an "outer" surface means that the surfaces faces away from the central axis, or is outboard of another "inner" surface. Terms such as "radial," "diameter," "circumference," etc. also are relative to the central axis.

The terms "front," "rear," "upper" and "lower" designate directions in the drawings to which reference is made.

As used herein, the proximal end of a prosthesis such as bifurcated stent graft is the end closest to the heart via the path of blood flow, whereas the distal end is the end furthest away (e.g., downstream of blood flow) from the heart during deployment. In contrast, the distal end of the catheter is usually identified to the end that is farthest from the operator (handle) while the proximal end of the catheter is the end nearest the operator (handle). However, those of skill in the art will understand that depending upon the access location, the stent graft and delivery system description may be consistent or opposite in actual usage.

The following detailed description is merely exemplary in nature and is not intended to limit the invention or the application and uses of the invention. Although the description is in the context of treatment of blood vessels such as the aorta, the teachings of this disclosure may also be used in any other body passageways where it is deemed useful, such as the coronary, carotid and renal arteries, etc.

Endovascular stent grafting, or endovascular aneurysm repair (EVAR), is a form of treatment for abdominal or thoracic aortic aneurysm that is less invasive than open surgery. Endovascular stent grafting uses an endovascular stent graft to reinforce the wall of the aorta and to help keep the damaged area from rupturing by excluding the aneurysm from blood flow. Stent grafts are generally tubular open-ended structures providing support for damaged, collapsing, or occluded blood vessels, such as the aorta. Stent grafts are flexible, which allows them to be inserted through, and conform to, tortuous pathways in the blood vessels. For example, stent grafts may be radially expandable from a radially-compressed (or radially-constricted) configuration for delivery to the affected vessel site to a radially-expanded configuration when deployed at the affected vessel treatment site, with the radially-expanded configuration having a larger diameter than the radially-compressed configuration. Stent grafts may be inserted in the radially compressed configuration and expanded to the radially-expanded configuration either through a self-expanding mechanism, or through the use of a balloon catheter, for example.

In one example, an EVAR procedure may include inserting a guide wire into a portion of the patient's body, such as the femoral artery. Once the guidewire is inserted into the artery, it may be gently pushed toward the site of the aneurism. A stent graft delivery system, which may include a catheter and stent graft, may be placed over the guidewire and inserted along the guidewire into the site of the aneurism. The stent graft may be guided within the catheter in its radially-compressed configuration and to the site of the aneurism. There may be radiopaque markers at a distal end of the stent graft delivery system or on the stent graft itself to allow the surgeon to guide the stent graft into the proper position. Once in proper position, the stent graft can be expanded from the radially-compressed configuration to the radially-expanded configuration. This can be done, for example, by pulling back a stent-graft cover, allowing the stent graft to expand due to its fabric being biased outwards. Once deployed into the radially-expanded configuration, the stent graft can be held in place with metallic hooks or stents. The catheter can then be removed, while the stent graft remains.

In some applications, the blood vessel wall or anatomical conduit in which the stent-graft is to be implanted is highly curved or angled. Moreover, packaging volume within the catheter may be limited.

Figure 1:
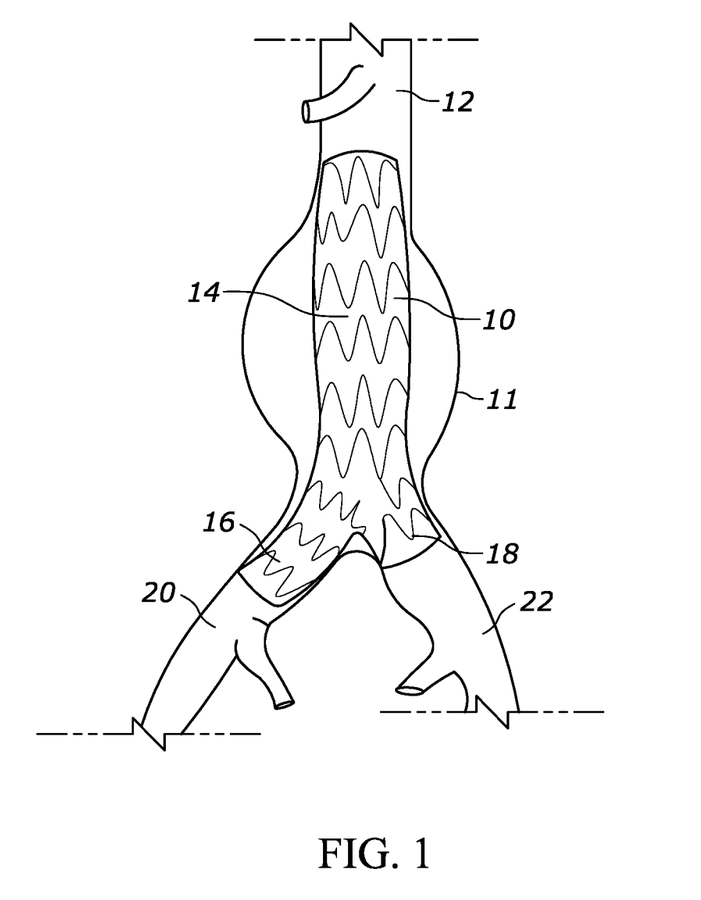
FIG. 1 is a side view of a stent graft installed into a blood vessel, for example an aorta, according to an embodiment.

FIG. 1 shows an example of a stent graft 10 in its installed, radially-expanded configuration within a blood vessel 12, in this case a patient's aorta, more particularly the abdominal aorta. Once affixed within the blood vessel 12, the stent graft 10 provides a tube or pipe for blood flow, guiding the blood flow through the stent graft 10. If the stent graft 10 is located within an aneurysm 11 of the blood vessel 12, the blood flow through the stent graft 10 may reduce the pressure within the aneurysm and allow it to reduce in size (regress) or remain stable. In one embodiment, graft material of the stent graft 10 is non-permeable, e.g., is polyester terephthalate (PET), expanded polyester terephthalate (ePET), polytetrafluoroethylene (PTFE), or other non-permeable graft material. As graft material is non-permeable, blood or other fluid is prevented from passing through graft material.

As shown in FIG. 1, the stent graft 10 may include main body 14, a first leg 16 extending from the main body 14, and a second leg 18 extending from the main body 14. The first leg 16 may be ipsilateral to where the initial guidewire was installed, and the second leg 18 that may be contralateral to the first leg 16, and may be shorter than the first leg 16. The first leg 16 may extend into a first iliac artery 20, while the second leg 18 may extend into a second iliac artery 22. The first and second legs 16, 18 may also guide blood flow therethrough, allowing those portions of the iliac arteries to heal, and removing stress from those regions of the arteries. A second stent graft may subsequently be inserted within and attached to either or both of the first and second legs 16, 18 to elongate the overall profile of the stent graft.

Figure 2A:
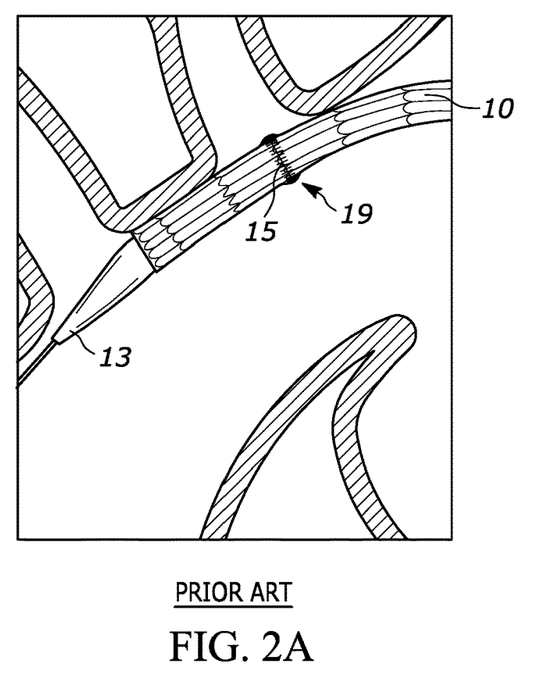
FIG. 2A is a cross-sectional view of a blood vessel with a stent graft in a radially-compressed configuration, according to one embodiment, illustrating a bunching of stitching along one transverse axis.
Figure 2B:
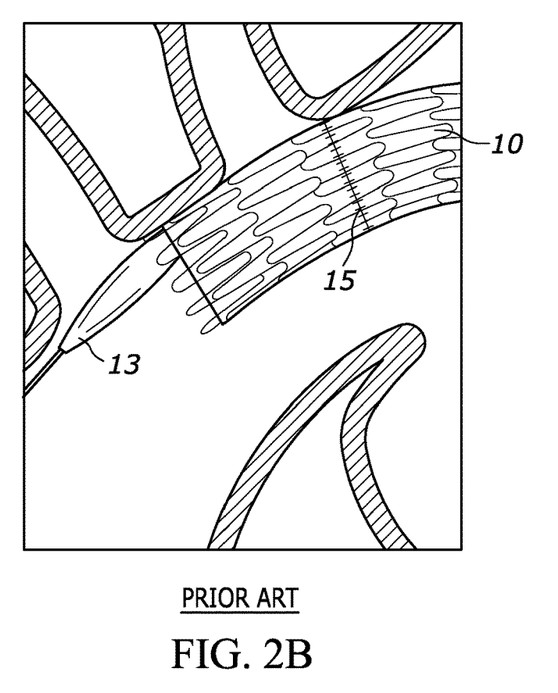
FIG. 2B is a cross-sectional view of the blood vessel of FIG. 2A with the stent graft in a radially-expanded configuration, according to an embodiment.

The first leg 16 may be connected to the main body 14 by stitching or a seam. Likewise, the second leg 18 may be connected to the main body 14 by stitching or a seam. When the stent graft 10 is in the radially-contracted configuration (e.g., during delivery into the patient's body), the seam at the interface between the main body 14 and the legs 16, 18 can bunch up. FIGS. 2A-2B illustrate this concept. In FIG. 2A, the stent graft 10 is shown being inserted into a blood vessel 12 with any outer catheter removed for illustrative purposes. The stent graft 10 is in its radially-contracted configuration and is guided through the blood vessel 12 via a guide 13. A plurality of stitches 15 (e.g., stitches that connect the main body 14 to one or both of the legs 16, 18) can form a seam that can create a bulge or bump 19 on the outer portion of the stent graft 10 during installation. This is due to the material of the stitches 15 being in close relative axial proximity. This may have a potential to reduce available space within the catheter during delivery, for example. While the bunch or bulge 19 of stitching material is gone when the stent graft 10 is in its radially-expanded configuration (as shown in FIG. 2B), the bunch or bulge 19 is nonetheless present during the insertion phase when the stent graft 10 is in its radially-contracted configuration (as shown in FIG. 2A).

Therefore, according to various embodiments described herein, a stent graft is provided with stitches or sutures that define an oblique stitch path. As used herein, the term "oblique" is intended to mean slanted, or angled by an angle other than a right angle or parallel angle. And, as used herein, the term "stitch path" or "seam path" is intended to mean an average or nominal direction of a group of stitches that form at least a seam. Of course, within each seam, a plurality of individual or localized stitches (e.g., a small group of stitches) may be oriented in different directions, but the "stitch path" in this disclosure is intended to mean an overall direction of a collective group of stitches; in other words, a nominal direction of the stitches. In one embodiment, a group of 30 to 100 stitches can collectively define a seam path, such that the seam path extends along a path that reflects the nominal direction of these 30 to 100 stitches.

Figure 3A:
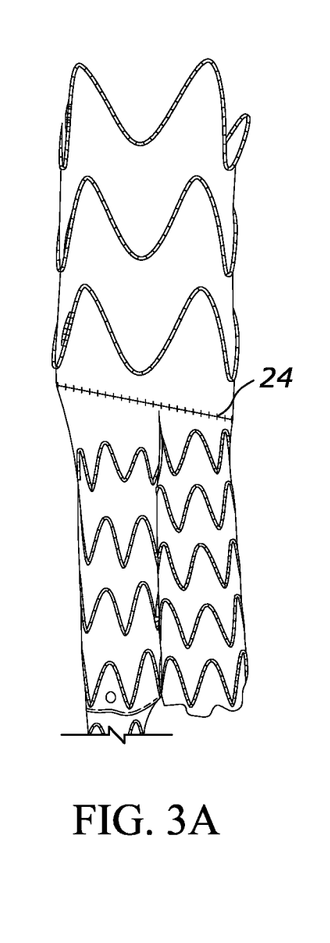
FIG. 3A is a front view of a stent graft with axially-offset seam, according to one embodiment.
Figure 3B:
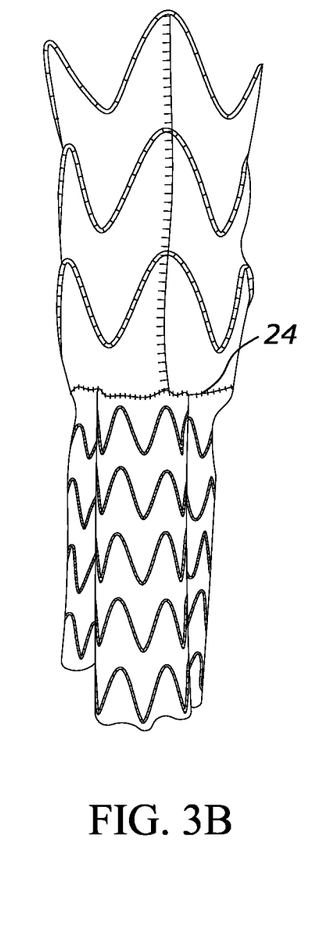
FIG. 3B is a side view of the stent graft of FIG. 3A.

A stent graft with an oblique seam path is generally shown in FIGS. 3A-3B, in which the stent graft has a seam 24 connecting the main body 14 to the legs 16, 18, wherein the seam 24 is oblique relative to the length of the stent graft, as will be described further below. While only two legs 16, 18 are shown in this Figure and FIG. 4, more than two legs may be provided. For example, three, four, or five legs may extend from the main body 14, and may be attached thereto via a seam. The stitching that joins the main body to at least one of the legs can be angled relative to a longitudinal axis of the main body and/or leg. This allows the stitching of the seam to be more dispersed along the length of the stent graft when the stent graft is in its radially-contracted configuration. This can remove or reduce the size of the bulge of the stitching explained above when in the radially-contracted configuration. By creating a seam that distributes the stitching or suture material along the length of the stent graft, packing of this material will occupy an effectively smaller cross-sectional area at a given axial location of the stent graft.

Figure 4:
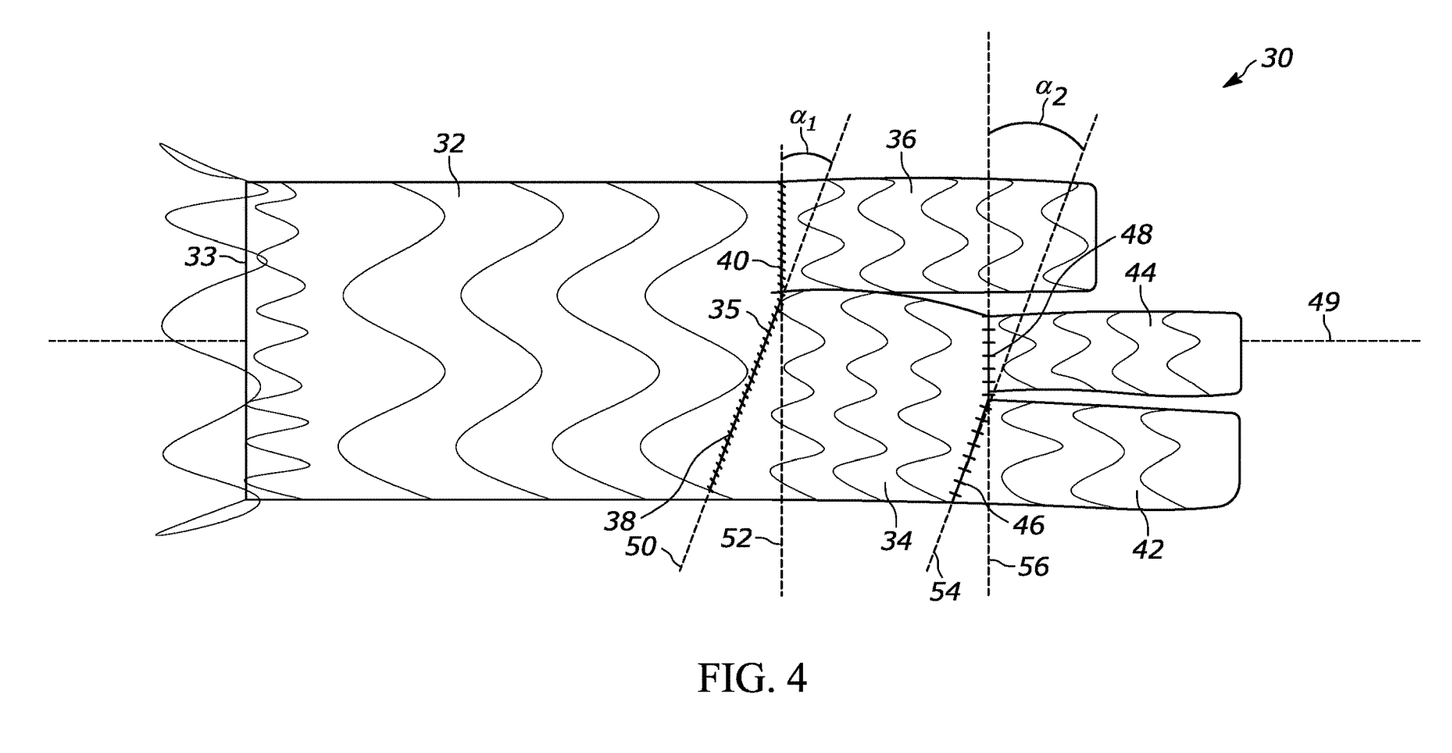
FIG. 4 is an overhead plan view of a stent graft with axially-offset seams joining various legs to other bodies of the stent graft, according to one embodiment.

Referring to FIG. 4, a stent graft 30 with such an oblique seam is shown according to one embodiment. The stent graft 30 may be used in abdominal aortic aneurysms (AAA), thoracoabdominal aortic aneurysms (TAAA), or any other aortic aneurysms where a splitting of blood flow into multiple lumens is desired. The stent graft 30 of FIG. 4 is shown in its radially-expanded configuration, not deployed inside a patient's body. The stent graft 30 has a main body 32 that extends from a proximal end 33 to a first leg 34 and a second leg 36 located at a distal end 35 of the main body 32. A first seam 38 joins the first leg 34 to the main body 32. A second seam 40 joins the second leg 36 to the main body 32. The first and second seams 38, 40 may be continuous, in that the stitching continues uninterruptedly in joining the first leg 34 to the main body 32, and in joining the second leg 36 to the main body 32. In one embodiment, the first leg 34 feeds into, or is connected to, a first tributary leg 42 and a second tributary leg 44 (which may also be called branch legs). Each of the tributary/branch legs 42, 44 are optional additions to the stent graft 30 for extending (directly or via additional extensions) into respective blood vessels (e.g., the renal, celiac, and/or SMA arteries). The second leg 36 may be a bypass leg to allow flow into the distal aorta. Therefore, in certain embodiments, a proximal end of the first leg 34 may be connected to the main body 32 via a seam or stitching, and a distal end of the first leg 34 may be connected to a first tributary leg 42 and a second tributary leg 44. A third seam 46 joins the first leg 34 to the first tributary leg 42, and a fourth seam 48 joins the first leg 34 to the second tributary leg 44. Each seam 38, 40, 46, 48 can include fabric, polymer, or metal stitching, for example. While the embodiment shown has two tributary legs, in other embodiments there may be three or more tributary legs. In another embodiment, second leg 36 may also have two or more tributary legs attached thereto.

As can be seen in FIG. 4, the main body 32 extends along a main longitudinal axis 49. Each of the legs 34, 36, 42, 44 extend along respective axes that are parallel to the main longitudinal axis 49 when the stent graft 30 is in the radially expanded configuration, not installed into various blood vessels in a patient. In other words, the stent graft 30 is shown in FIG. 3 in a preinstalled configuration in which the stent graft 30 is not yet compacted or compressed to fit within a catheter for insertion into a body of a patient.

Each seam includes a plurality of stitches that extend along a stitch path. For example, the first seam 38 includes a first plurality of stitches that extend along a first stitch path 50, also referred to as a seam path or seam axis. Likewise, the second seam 40 includes a plurality of stitches that extend along a second stitch path 52. At least one or both of the stitch path axes 50, 52 can extend at an angle that is oblique relative to the longitudinal axis 49 and to a normal axis that is normal or perpendicular to the axis 49. In the embodiment shown in FIG. 4, only the first stitch path 50 is oblique relative to the longitudinal axis 49. However, in other embodiments, the second stitch path 52 extends parallel or colinear with the first stitch path 50 and oblique relative to the longitudinal axis 49. In still other embodiments, both the first and second stitch paths 50, 52 may be oblique to the longitudinal axis 49, but at different angles. In another embodiment, the second stitch path 52 may be oblique to the longitudinal axis 49, while the first stitch path 50 is normal to it.

In one embodiment, the first stitch path 50 and the second stitch path 52 form an angle $\alpha_1$ that is acute. In one embodiment, $\alpha_1$ is between 5-20 degrees, and can in more particular embodiments be between 5-10 degrees. This would yield an acute angle between the first stitch path 50 and the longitudinal axis 49 of between 70-85 degrees, and between 80-85 degrees in the respective embodiments. These angles allow the stitching to be spread along the axial direction of the stent graft 30 to reduce or remove the prevalence of the bulge or bump of stitching material in the radially-compressed configuration without increasing the length of the seam to an undesirable amount that might reduce strength and increase material usage.

By providing at least one stitch path 50, 52 that extends in an oblique direction relative to the longitudinal axis 49, the stitching between the main body 32 and at least one of the legs 34, 36 is spread out along the length of the stent graft 30. Therefore, when the stent graft 30 is in its radially-compressed configuration, the stitches do not coalesce to such a degree that a bulge or bump on the exterior profile of the stent graft 30 would hinder packaging or movement of the stent graft 30 within a catheter (as described above with reference to FIGS. 2A-2B). As explained herein, in some embodiments only one stitch path 50 is oblique to the longitudinal axis. This stitch path is located at the joining of the main body 32 to the first leg 34, which may be wider than the second leg 36. By having an oblique stitch path at the joining between the main body at the larger of the two legs, the stitching can be spread out along a portion of the length of the stent graft where a large amount of stitching may otherwise bunch up due to the relatively large width of the first leg 34.

Referring to FIG. 4, one or more of the seams connecting the first leg 34 to the tributary legs 42, 44 can be oblique to the longitudinal axis 49. In particular, in an embodiment, the third seam 46 includes a third plurality of stitches that extend along a third stitch path 54, and the fourth seam 48 includes a fourth plurality of stitches that extend along a fourth stitch path 56. Like the first and second seam axes 50, 52, the third seam axis 54 can be angled relative to the third seam axis 56. For example, the fourth seam axis 56 can extend in a direction normal to the longitudinal axis 49, while the third seam axis 54 can extend in a direction oblique to the fourth seam axis 56. In other embodiments, both axes 54, 56 extend in an oblique direction to the longitudinal axis 49. In still other embodiments, both the third and fourth seam axes 54, 56 may be oblique to the longitudinal axis 49, but at different angles. In another embodiment, the fourth seam axis 56 may be oblique to the longitudinal axis 49, while the third seam axis 54 is normal to it. The third stitch path 54 and the fourth stitch path 56 can intersect at an angle $\alpha_2$ that may be similar or equal to $\alpha_1$.

By providing at least one stitch path 54, 56 that extends in an oblique direction to the longitudinal axis 49, the stitching between the first leg 34 and at least one of the tributary legs 42, 44 is spread out along the length of the stent graft 30. Therefore, when the stent graft 30 is in its radially-compressed configuration, the stitches do not coalesce to such a degree that a bulge or bump on the exterior profile of the stent graft 30 would hinder packaging or movement of the stent graft 30 within a catheter.

Figure 5:
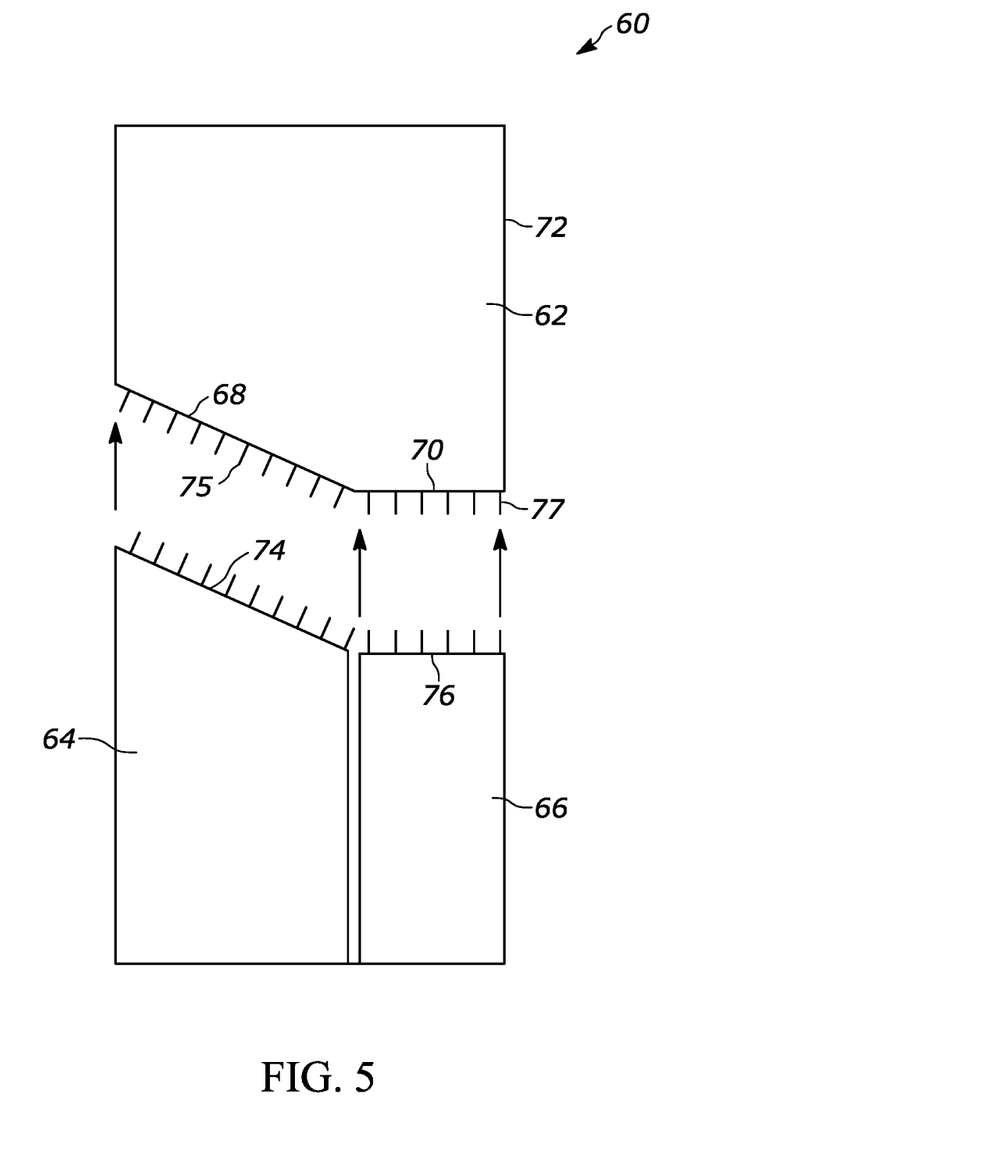
FIG. 5 is a schematic view of fabric cutting and stitching along two different axes of the same stent graft, according to one embodiment.

FIG. 5 illustrates a plan view of fabric 60 that is cut to shape and stitched together to form the shape of the stent graft 30. The fabric 60 can be non-permeable, such as polyester terephthalate (PET), expanded polyester terephthalate (ePET), polytetrafluoroethylene (PTFE), or other non-permeable graft material. The fabric may include a first fabric portion 62 that eventually forms the main body 32, a second fabric portion 64 that eventually forms the first leg 34, and a third fabric portion 66 that eventually forms the second leg 36.

At the distal end of the fabric 60, the first fabric portion 62 includes a first edge 68 and a second edge 70. The second edge 70 extends generally perpendicular to a longitudinal edge 72 of the first fabric portion 62. This allows the main body 32 to have a portion of its axial end to extend generally perpendicular to the longitudinal axis 49. However, unlike the second edge 70, the first edge 68 extends along a direction that is offset or angled (e.g., not perpendicular) to the second edge 70 and the longitudinal edge 72. The second fabric portion 64 has a corresponding proximal edge 74 that is offset or angled to match the shape of the first edge 68. Stitching 75 or the like can attach the proximal edge 74 of the second fabric portion 64 to the first edge 68 of the first fabric portion 62. This forms the first leg 34 having an offset seam axis 50. The third fabric portion 66 has proximal edge 76 that corresponds in shape to the second edge 70 of the first fabric portion 62. Once again, stitching 77 or the like can attach the proximal edge 76 to the second edge 70. This forms the second leg 36 having a seam axis 52 that is angled relative to the seam axis 50.

While exemplary embodiments are described above, it is not intended that these embodiments describe all possible forms encompassed by the claims. The words used in the specification are words of description rather than limitation, and it is understood that various changes can be made without departing from the spirit and scope of the disclosure. As previously described, the features of various embodiments can be combined to form further embodiments of the invention that may not be explicitly described or illustrated. While various embodiments could have been described as providing advantages or being preferred over other embodiments or prior art implementations with respect to one or more desired characteristics, those of ordinary skill in the art recognize that one or more features or characteristics can be compromised to achieve desired overall system attributes, which depend on the specific application and implementation. These attributes can include, but are not limited to cost, strength, durability, life cycle cost, marketability, appearance, packaging, size, serviceability, weight, manufacturability, ease of assembly, etc. As such, to the extent any embodiments are described as less desirable than other embodiments or prior art implementations with respect to one or more characteristics, these embodiments are not outside the scope of the disclosure and can be desirable for particular applications.

What is claimed is:

1. A stent graft expandable from a radially-collapsed configuration to a radially-expanded position, the stent graft comprising:
   a main body defining a single lumen extending along a main longitudinal axis and having a proximal end and a distal end, wherein the distal end defines a perimeter in which the main body is coupled with a first leg and a second leg; and
   a plurality of stitches coupling the main body to the first leg, the plurality of stitches forming a stitch path around the perimeter of the distal end of the main body that extends in a direction oblique with respect to a longitudinal axis passing through a location where the first and second legs meet when the stent graft is in a preinstalled configuration prior to insertion into a body of a patient.

2. The stent graft of claim 1, further comprising a second plurality of stitches coupling the main body to the second leg, the second plurality of stitches forming a second stitch path, at least a portion of which being oblique to the first stitch path.

3. The stent graft of claim 2, wherein the second stitch path is perpendicular to the main longitudinal axis when the stent graft is in the preinstalled configuration.

4. The stent graft of claim 1, wherein the first leg has a proximal end connected to the distal end of the main body, and the first leg has an opposing distal end, wherein the stent graft further includes a tributary leg connected to the distal end of the first leg.

5. The stent graft of claim 4, further comprising a second plurality of stitches connecting the distal end of the first leg to the tributary leg, the second plurality of stitches extending along a second stitch path that is oriented at an acute angle relative to the main longitudinal axis of the main body.

6. The stent graft of claim 5, further comprising a second tributary leg connected to the distal end of the first leg, and a third plurality of stitches connecting the distal end of the first leg to the second tributary leg.

7. The stent graft of claim 6, wherein the third plurality of stitches extend along a third stitch axis that is oriented at an angle relative to the second stitch axis.

8. The stent graft of claim 5, wherein the acute angle is in a range between 70 to 85 degrees.

9. The stent graft of claim 8, wherein the acute angle is in a range between 80 to 85 degrees.

10. A stent graft comprising:
    a main body extending along a main longitudinal axis and having a proximal end and a distal end, wherein the distal end defines a perimeter in which the main body is coupled with a first leg and a second leg,
    the first leg is attached to the distal end of the main body along a first seam that extends around the perimeter along a first seam path; and
    the second leg is attached to the distal end of the main body along a second seam that is continuous with the first seam and extends along a second seam path, wherein the first seam path is oblique relative to the second seam path when the stent graft is in a preinstalled configuration prior to insertion into a body of a patient, and wherein the first seam path is oblique with respect to a longitudinal axis passing through a location where the first leg and the second leg meet.

11. The stent graft of claim 10, wherein the second seam path extends perpendicular to the main longitudinal axis, and the first seam path extends at an acute angle relative to the main longitudinal axis.

12. The stent graft of claim 10, wherein the angle between the first seam path and the second seam path is between 5-20 degrees.

13. The stent graft of claim 10, wherein the first leg has a proximal end connected to the distal end of the main body, and the first leg has an opposing distal end, wherein the stent graft further includes a tributary leg connected to the distal end of the first leg.

14. The stent graft of claim 13, further comprising a third seam connecting the distal end of the first leg to the tributary leg, the third seam extending along a third seam path that is oriented at an acute angle relative to the main longitudinal axis of the main body.

15. The stent graft of claim 14, further comprising a second tributary leg connected to the distal end of the first leg by a fourth seam that extends along a fourth seam path angled relative to the third seam path.

16. The stent graft of claim 10, wherein the first leg is wider than the second leg.

17. A stent graft comprising:
 a main body extending along a longitudinal axis when the stent graft is in a preinstalled configuration prior to insertion into a body of a patient, the main body having an axial end;
 a first leg attached to and extending axially from the axial end of the main body in a direction parallel to the longitudinal axis;
 a second leg attached to and extending axially from the axial end of the main body in a direction parallel to the longitudinal axis, the second leg being narrower than the first leg; and
 a plurality of stitches coupling the main body to the first leg, the plurality of stitches forming a stitch path that extends in a direction oblique with respect to a longitudinal axis passing through a location where the first leg and the second leg meet, the first and second legs being separate from the main body prior to attachment to the main body.

18. The stent graft of claim 17, wherein the second plurality of stitches forming a second stitch path that extends in a direction that is oblique to the first stitch path.

19. The stent graft of claim 17, wherein the first leg includes an axial end, and wherein the stent graft further includes first and second tributary legs extending from the axial end of the first leg.

20. The stent graft of claim 19, wherein the first tributary leg is coupled to the first leg via a third plurality of stitches that form a third stitch path, wherein the second tributary leg is coupled to the first leg via a fourth plurality of stitches that form a fourth stitch path, and wherein the third stitch path and the fourth stitch path are angled relative to each other.

* * * * *